United States Patent [19]

Fumino

[11] Patent Number: 4,694,850
[45] Date of Patent: Sep. 22, 1987

[54] GAS SUPPLY MECHANISM

[75] Inventor: Ichiro Fumino, Tokyo, Japan

[73] Assignee: Nippon Tansan Gas Co., Ltd., Tokyo, Japan

[21] Appl. No.: 916,233

[22] Filed: Oct. 7, 1986

[30] Foreign Application Priority Data

Oct. 11, 1985 [JP] Japan .......................... 60-154352[U]
Nov. 19, 1985 [JP] Japan .......................... 60-176841[U]
Mar. 27, 1986 [JP] Japan ................................. 61-67193

[51] Int. Cl.$^4$ .......................... F16K 51/00; B67B 7/24
[52] U.S. Cl. ................................ 137/318; 137/505.42;
222/5; 222/82
[58] Field of Search ............... 137/318, 505.42; 222/5,
222/82

[56] References Cited

U.S. PATENT DOCUMENTS

| | | | |
|---|---|---|---|
| 2,016,113 | 10/1935 | Lambert et al. | 222/5 |
| 2,021,603 | 11/1935 | Kelly, Jr. et al. | 222/5 |
| 2,709,065 | 5/1955 | Pohndorf | 137/505.42 |
| 2,768,643 | 10/1956 | Acomb | 137/505.42 |
| 3,269,598 | 8/1966 | Butters et al. | 222/5 |
| 3,319,829 | 5/1967 | Sentz | 222/5 |
| 3,325,053 | 6/1967 | De Boer et al. | 222/82 |
| 3,352,456 | 11/1967 | Swineford | 222/5 |
| 3,682,437 | 8/1972 | Miller | 137/505.42 |
| 3,776,227 | 12/1973 | Pitesky et al. | 222/5 |
| 4,370,997 | 2/1983 | Braithwaite et al. | 222/5 |

FOREIGN PATENT DOCUMENTS

| 834927 | 5/1960 | United Kingdom | 222/82 |
|---|---|---|---|
| 1507839 | 4/1978 | United Kingdom | 137/318 |

Primary Examiner—George L. Walton
Attorney, Agent, or Firm—Lackenbach Siegel Marzullo & Aronson

[57] ABSTRACT

The gas supply mechanism includes a main body, a nut, a packing having an O-ring part and a ringlike flange part, a piercing body and a valve housing. The O-ring part fits well the sealing cover of a gas cartridge even if the surface of the sealing cover is not flat. The valve housing has a gas passage and a bypass which enables to prevent pulsation of gas flow.

5 Claims, 7 Drawing Figures

GAS SUPPLY MECHANISM

BACKGROUND OF THE INVENTION

1. Field of the Invention

The present invention relates to a mechanism that gets a gas from a high pressure gas cartridge and that supplies a constant amount of gas per time. This mechanism is effective especially when adopted in such devices as oxygen inhalers or gas burners, in which pulsating of gas is not desirable.

2. Description of the Prior Art

If a surface of a sealing cover of a gas cartridge is flat, a ringlike flat packing has only to be adopted in order to prevent gas leakage when the sealing cover is pierced.

However, if the surface of the sealing cover is not flat as in a calked sealing cover, the neck of the cartridge has to be sealed by an O-ring in addition to the ringlike flat packing. This type of sealing has some demerits. For example, the space between the sealing cover and the packing becomes full of a leaked gas, which exerts a high pressure onto the surface of a sealing cover and presses the O-ring to the periphery of the cartridge. These prevent the cartridge from being moved to a place where the sealing cover can be pierced completely. Therefore, the sealing cover can not be pierced completely, so that lesser amount of gas is supplied as the amount of gas in the cartridge decreases.

A valve pin and a sealing member co-operate to modulate the amount of gas supply. In these devices a gas pressure is not be exerted onto the outer periphery of the sealing member. However, the pressure onto the inner periphery of the sealing member varies while the gas is flowing through the interval between the valve pin and the sealing member, being affected by consumed amount of gas. Therefore, the sealing member is often distorted to vary the interval between the valve pin and the sealing member. Consequently, it is impossible to keep the amount of gas flowing through the interval constant.

SUMMARY OF THE INVENTION

An object of this invention is to present a mechanism supplying a constant amount of gas per time which has a packing to prevent gas leakage by fitting the sealing cover of a high pressure gas cartridge in a gas tight fashion when the sealing cover is pierced.

The other object of this invention is to present a mechanism supplying a constant amount of gas per time which has a sealing member and a valve pin that can keep a certain interval therebetween while the gas flows through the interval.

DETAILED DESCRIPTION OF THE INVENTION

Figure 1:
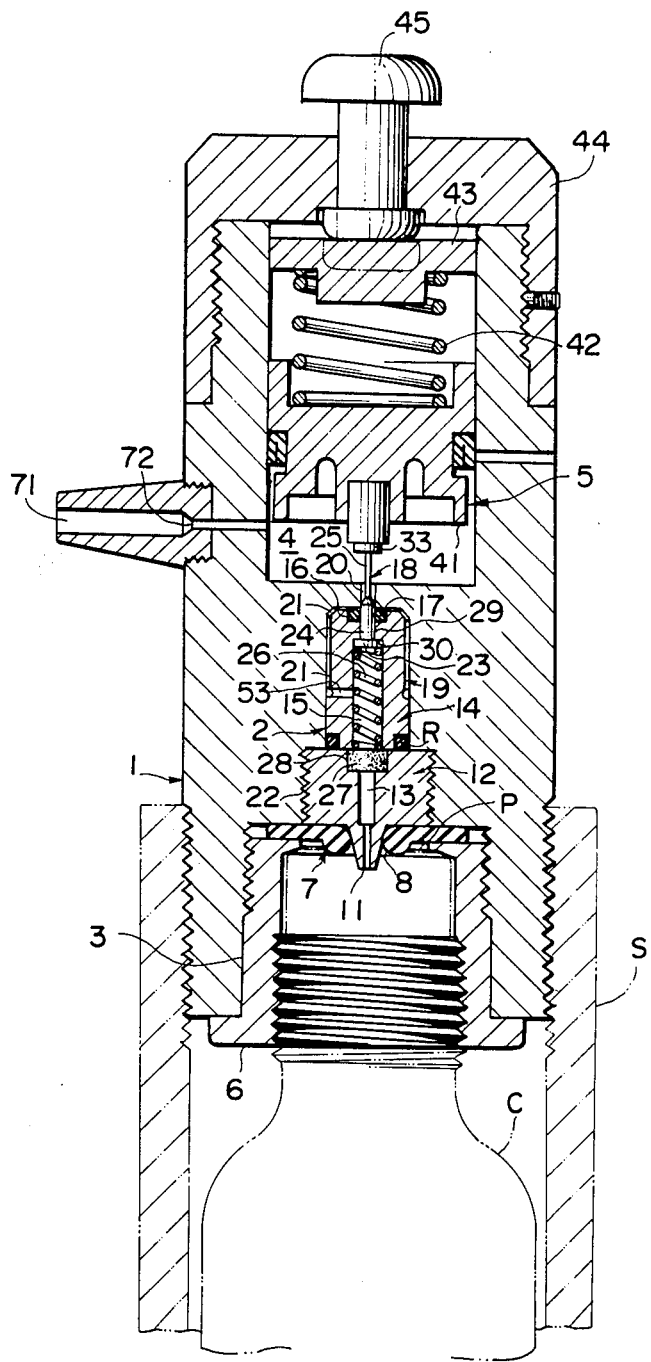
FIG. 1 is a sectional side-view of an embodiment of a gas supply mechanism of this invention.
Figure 2:
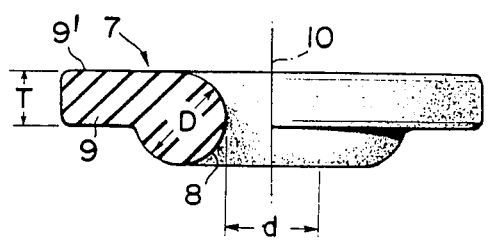
FIG. 2 is an enlarged half-sectional view and FIG. 3 is a bottom view of an embodiment of a packing.

In the drawings the same numerals or characters cover the same of similar parts.

A main body 1 has a hole 2 therethrough on the axial line thereof. The hole 2 has a socket 3 for a pressure cartridge C on one end thereof, and has a second pressure chamber 4 with a pressure modulating mechanism 5 on the other end thereof.

The pressure modulating mechanism 5 is of an ordinary type with a piston 41, a modulating spring 42, a spring seat 43 and a spring pressure modulating cover 44.

A gas can flow out through a first portion 20 when a button 45, which is equipped through the cover 44, is pushed down to push the spring seat 43 downwards. A nut 6 is screwed into the socket 3 to settle a packing 7. The packing 7 has an O-ring part 8 and a flat ringlike flange part 9 on the periphery thereof. The O-ring part 8 and the flange part 9 co-operate to make a flat plane 9' which is at a right angle with the packing's axial line 10.

The flange part has a thickness T which is shorter than a diameter D of a cross section of the O-ring part.

A leaked gas pressures an area of a surface of a sealing cover P of a cartridge C. The area is defined by a needle 11 and the O-ring part 8, so that the area can be narrowed by shortening an inner diameter d of the O-ring part 8. When the O-ring part 8 is in contact with the needle 11 in a gas tight fashion, the sealing cover P is easily pierced by the needle 11.

The packing 7 is of elastic material, such as rubber, resin and so on.

A piercing body 12 has the needle 11 projecting downwards for piercing the sealing cover P. The piercing body 12 inclusive of the needle 11 has a gas passage 13 therethrough on the axial line thereof. A valve housing 14 has a gas passage 15 therethrough on the axial line thereof.

There is formed a cavity 16 around the passage 15 at one end of the passage 15. A sealing member 17 is settled in the cavity 16. The sealing member 17 can open and close the passage 15 by co-operating with a valve pin 18, which is given a tendency by a spring 26 to move upward and a part of which is in the chamber 4. An outer periphery of the cavity 16 communicates with the passage 15 through a bypass 19.

The hole 2 of the main body 1 has three portions 20, 21 and 22 midway therethrough. The first portion 20 connects with the second pressure chamber 4. The valve pin 18 moves through the first portion 20.

The second portion 21 connects with and has a longer diameter than the first portion 20, and receives the valve housing 14. The portion 22 connects with and has a longer diameter than the second portion 21, and the piercing body 12 screws thereinto.

The packing 7 is settled in the main body 1 by the nut 6 with its flat plane 9' on the piercing body 12 and with its O-ring part 8 around the needle 11.

The valve pin 18 has flange 23, a larger diameter portion 24 and a narrower diameter portion 25 in order.

The flange 23 and the larger diameter portion 24 are inserted into the passage 15, that is a first gas pressure chamber. The valve pin 18 is always pushed upward by the spring 26 which is set between the flange 23 and a filter 27. The filter 27 is inserted into a larger diameter part 28 at the top end of the gas passage 13 of the piercing body 12.

The valve pin 18 can move upward until when the flange 23 meets a step 30 which is at the lowest part of the a shorter diameter part 29 which fits an upper first portion 20 of the passage 15.

When the flange 23 meets the step 30 the larger diameter portion 24 comes in contact with an inner surface 32 (FIG. 4) of the sealing member 17 to stop gas flow. The valve pin 18 co-operates with the sealing member 17 to make and cut off connections between the first pressure chamber 15 and the second pressure chamber 4.

It is desirable that the narrower diameter portion 25 inclines to the larger diameter portion 24. In order to prevent the inner surface's being injured by the valve 18 when it moves upward or downward. It is possible to form a flange 33 at the top of the valve pin 18 to get pressure from the piston 41.

The bypass 19 has at least one vertical gutter 51 formed on the outer periphery of the valve housing 14, at least one horizontal gutter 52 formed on the top of the valve housing 14 connecting one end of the gutter(s) 51 with the outer periphery of the cavity 16, and at least one horizontal passage 53 connecting the other end of the gutter(s) 51 with the gas passage 15.

Figure 5:
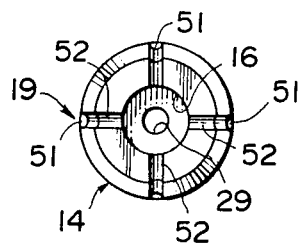
FIG. 4 is an enlarged half-sectional view and FIG. 5 is a plan view without a sealing member of an embodiment of a valve housing.
Figure 4:
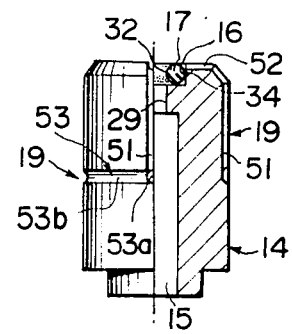
Figure 3:
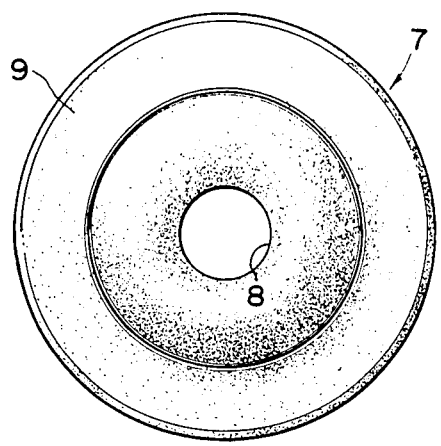

In an embodiment illustrated in FIGS. 1, 4 and 5, the bypass 19 comprises four horizontal gutters 52, four vertical gutters 51 and one horizontal passage 53 comprising a horizontal hole 53a and a ringlike gutter 53b. The ringlike gutter 53b is formed on a periphery of the valve housing 14, and communicates with the horizontal hole 53a and the vertical gutters 51. Each vertical gutter 51 being at the same distance from its neighbor vertical gutters 51. The horizontal gutters 52 are radially arranged and communicate with the outer periphery of the cavity 16 at four places. Each place being at the same distance from its neighbor places. In this construction, the gas presses each part of the sealing member 17 evenly, so that distortion of the sealing member 17 can be prevented more certainly. The bypass can be formed quite easily on and in the valve housing 14.

Figure 7:
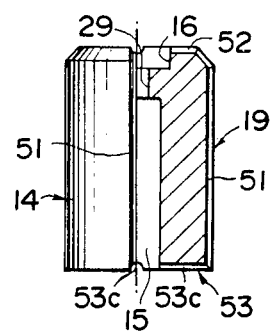
FIG. 7 is a plan view of another embodiment of a valve housing.
Figure 6:
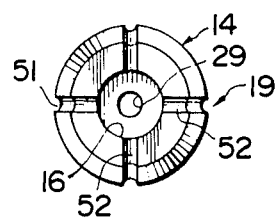
FIG. 6 is a half-sectional side-view.

Another embodiment illustrated in FIGS. 6 and 7 is different from the embodiment in FIGS. 1, 4 and 5 in these points described hereinafter. In this embodiment, such an O-ring as the O-ring R in FIG. 1 is omitted. The horizontal passages 53 are four horizontal gutters 53c that are formed on the bottom of the valve housing 14. The horizontal gutters 53c communicates with vertical gutters 51 which are formed from the top to the bottom of the valve housing 14. In this embodiment the bypass 19 can be formed more easily.

If the cartridge C has a male screw on its neck, the cartridge C can be screwed into the nut 6 which has a female screw. If the cartridge C has no screw thereon, a male screw is formed on the lower periphery of the main body 1, and a case S, which receives a cartridge C, is screwed on the main body 1.

In FIG. 1, 71 is an outlet of gas and the outlet 71 is connected with the second pressure chamber 4 by means of an aperture 72.

Operation

The operation of an embodiment where the cartridge C has a male screw on its neck is described hereinafter. As the cartridge C is screwed into the nut 6, the sealing cover P is pierced by the needle 11, and then the upper surface of the sealing cover P is pressed on the O-ring part 8 of the packing 7. At this time some of a gas from the cartridge C leaks out in the space surrounded by the O-ring part 8, the piercing body 12 and the sealing cover P. But the gas pressure on the upper surface of the sealing cover is not so high as to prevent the cartridge C from being easily screwed into the nut 6 further until it comes in the position where the sealing cover P is completely pierced. A constant amount of gas per time flows out from the outlet 71, as the gas pressure is modulated in the second pressure chamber 4.

If the inner diameter d is nearly equal to the outer diameter of the needle 11, the area of the upper surface of the sealing cover P on which the leaked gas puts pressure is very narrow, so that the cartridge C can very easily be screwed into the nut 6. When the valve pin 18 is pushed downward the gas flows from the first pressure chamber 15 to the second pressure chamber 4. At that time the gas exerts pressure on the inner surface 32 of sealing member 17, so that the inner surface 32 is going to distort outward. But, some of the gas in the passage 15 exerts pressure on the outer surface 34 through the bypass 19. Consequently, the pressure on the inner surface 32 balances with the pressure on the outer surface 34, so that the distortion of the sealing member 17 can be prevented. The narrower diameter portion 25 of valve pin 18 therefore keeps a certain interval separation from the surface 32, so that a constant amount of gas per time flows through this interval separation space into the second pressure chamber 4.

I claim:

1. A gas supply mechanism comprising a main body which has a hole therethrough on the axial line thereof containing a socket for a pressure cartridge on one end thereof and a second pressure chamber with a pressure modulating mechanism on the other end thereof, a nut screwed into said socket and around a top portion of said pressure cartridge to settle a packing disposed between the main body and said cartridge top portion, said packing having an O-ring part and a flat ringlike flange part on the periphery thereof, a piercing body having a needle projecting downwardly and into engagement with said packing at said cartridge top portion, said needle having a gas passage therethrough on the axial line thereof, a valve housing having a gas passage therethrough on the axial line thereof and having a cavity in which a sealing member is settled and an outer periphery on which communicates with said gas passage through a bypass at one end of and around said gas passage; said hole in said body comprising midway therethrough a first portion which communicates with the second pressure chamber and through which a valve pin moves, a second portion which communicates with said first portion and which receives said valve housing, and a third portion which communicates with said second portion and into which said piercing body screws; said valve pin co-operating with said sealing member to make and cut off connections between said gas passage and said second pressure chamber, said packing being settled in said main body by said nut with its flange part on said piercing body and with its O-ring part being deformed around said needle and into engagement with said cartridge top portion when said needle pierces said cartridge top portion, to thereby provide an effective seal between said needle and said cartridge top portion.

2. The gas supply mechanism defined in claim 1, wherein said O-ring part is in contact with said needle in a gas tight fashion.

3. The gas supply mechanism defined in claim 1 or 2, wherein said bypass has at least one vertical gutter formed on the outer periphery of said valve housing, at least one horizontal gutter formed on top of the valve housing connecting said at least one vertical gutter with the outer periphery of the cavity, and at least one horizontal passage connecting said at least one vertical gutter with said gas passage.

4. The gas supply mechanism defined in claim 3, wherein said at least one horizontal gutter communicates with the outer periphery of said cavity at a plurality of places, each of which being at the same distance from its neighbor places, and said horizontal passage comprises a horizontal hole formed in said valve housing and a ringlike gutter that is formed on a periphery of said valve housing and that communicates with said horizontal hole and said at least one vertical gutter.

5. The gas supply mechanism defined in claim 3, wherein said at least one horizontal gutter communicates with the outer periphery of said cavity at a plurality of places, each of which being at the same distance from its neighbor places, and said at least one horizontal passage is formed on the bottom of said valve housing.

* * * * *